(12) United States Patent
Brieger et al.

(10) Patent No.: US 8,505,534 B2
(45) Date of Patent: Aug. 13, 2013

(54) HUMIDIFYING DEVICE FOR BREATHING GASES

(75) Inventors: Kai Brieger, Hamburg (DE); Thomas Rossen, Lübeck (DE); Markus Kämer, Gross Grönau (DE); Ludger Tappehorn, Lübeck (DE)

(73) Assignee: Dräger Medical GmbH, Lübeck (DE)

( * ) Notice: Subject to any disclaimer, the term of this patent is extended or adjusted under 35 U.S.C. 154(b) by 414 days.

(21) Appl. No.: 12/706,240

(22) Filed: Feb. 16, 2010

(65) Prior Publication Data
US 2010/0242963 A1 Sep. 30, 2010

(30) Foreign Application Priority Data
Mar. 30, 2009 (EP) .................................... 09156682

(51) Int. Cl.
*F23D 11/00* (2006.01)
(52) U.S. Cl.
USPC .................................................... 128/203.26
(58) Field of Classification Search
USPC .................. 604/23, 26; 128/203.16, 203.17, 128/203.27, 204.13, 204.22, 204.23, 203.26
See application file for complete search history.

(56) References Cited

U.S. PATENT DOCUMENTS

| 4,014,010 A | 3/1977 | Jinotti |
| 6,272,933 B1 | 8/2001 | Gradon et al. |
| 2003/0098022 A1 | 5/2003 | Nakao et al. |
| 2006/0213515 A1* | 9/2006 | Bremner et al. ......... 128/204.17 |
| 2009/0090363 A1* | 4/2009 | Niland et al. ............ 128/203.26 |

FOREIGN PATENT DOCUMENTS

| DE | 26 44584 | 4/1978 |
| DE | 693 23 518 T2 | 6/1999 |
| EP | 0 589 429 A1 | 3/1994 |
| WO | WO 2008/148154 A1 | 12/2008 |

* cited by examiner

*Primary Examiner* — Theodore Stigell
(74) *Attorney, Agent, or Firm* — McGlew and Tuttle, P.C.

(57) ABSTRACT

A humidifying device for breathing gases. The humidifying device has a housing with a recess, a heater, an evaporating chamber with a water feed, a breathing gas feed channel, a breathing gas outlet channel and at least one float element and at least one filling level indicator. The evaporating chamber can be introduced at least partially into the recess and is in contact with the heater to heat water and is designed to receive water from a water reservoir through the water feed. The at least one float element is guided in a floatingly movable manner on the water and is designed to close the feed of water above a water level set point in the evaporating chamber, and the at least one filling level indicator is designed to recognize the drop of the water level from the water level set point as a function of the position of the at least one float element.

25 Claims, 6 Drawing Sheets

HUMIDIFYING DEVICE FOR BREATHING GASES

CROSS REFERENCE TO RELATED APPLICATIONS

This application claims the benefit of priority under 35 U.S.C. §119 of European Patent Application EP 09 156 682.8 filed Mar. 30, 2009, the entire contents of which are incorporated herein by reference.

FIELD OF THE INVENTION

The present invention pertains to a humidifying device for breathing gases and to a process for operating a humidifying device for breathing gases.

BACKGROUND OF THE INVENTION

Artificial respiration of patients is carried out according to the state of the art by means of respirators which send a breathing gas according to the positive pressure method to the patient. The breathing gas is either drawn in by a fan from the environment or it enters a humidifying device from a central gas supply system. Humidifying devices are used during the respiration of a patient to add water vapor to the breathing gas fed to the patient during each phase of inspiration in order to humidify the essentially dry breathing gas drawn in from the environment or introduced from the central gas supply system in a temperature-controlled manner or to an extent at or close to full moisture saturation.

Such a humidifying device is known from U.S. Pat. No. 6,272,933 B1. The humidifying device contains a refillable evaporating chamber, which is intended to receive water that is to be evaporated. The evaporating chamber is arranged in contact with a heater within a housing. The evaporating chamber contains a water feed means, into which water enters under the force of gravity from a water reservoir through an opening. Furthermore, breathing gas, which will be heated and humidified in the evaporating chamber, enters through another opening into the evaporating chamber. The water reserve in the evaporating chamber may be used up rapidly during the respiration of the patients, which often lasts for days, with a corresponding humidification of the breathing gas. A necessary refilling of the water in the evaporating chamber is carried out according to the state of the art continuously by means of a valve technique developed especially for this purpose, as it is described, for example, in DE 693 23 518 T2. However, automatic filling of the evaporating chamber with water is limited because of the limited volume of the water reservoir, as a result of which further humidification of the breathing gases cannot take place any longer when the water in the reservoir has been consumed.

A solution to this problem is described in U.S. Pat. No. 6,272,933 B1, according to which the data of a temperature sensor arranged on the breathing gas outlet channel of the evaporating chamber and of a measured signal of the breathing gas flow through the chambers are analyzed. An algorithm determines from this a state of the evaporating chamber without water. The drawback of this solution is, however, the fact that an alarm can only be triggered with a time delay, namely, after the analysis has been concluded, as a consequence of which the course of a therapy may be possibly affected.

SUMMARY OF THE INVENTION

The object of the present invention is to eliminate the above-mentioned drawbacks. This object is accomplished by a device and a process according to the present invention.

A humidifying device for breathing gases according to the present invention is characterized in that the humidifying device comprises a housing with a recess, a heater, an evaporating chamber with a water feed means, a breathing gas feed channel, a breathing gas outlet channel and at least one float element and at least one filling level indicator, wherein said evaporating chamber can be introduced at least partially into said recess, is in contact with the heater for heating water and is designed to take up water from a water reservoir through the water feed means, wherein the at least one float element is guided in a floatingly movable manner on the water and is designed to close the water feed means above a water level set point in the evaporating chamber, and the at least one filling level indicator is designed to recognize lowering of the water from the water level set point as a function of the position of the at least one float element.

The humidifying device according to the present invention for breathing gases can advantageously signal a water shortage in the evaporating chamber early, so that a water reservoir can be replaced or refilled to fill up the evaporating chamber.

The filling level indicator is preferably designed corresponding to an embodiment of the present invention as an optical sensor array, which comprises a light transmitter and a light receiver and is adapted to the water level set point. The evaporating chamber is made in one piece from a transparent material, preferably a PU (polyurethane). The optical sensor array may thus advantageously also be arranged outside the evaporating chamber and inside the housing of the humidifying device and set up such that a light beam sent by the light transmitter into the evaporating chamber is interrupted by the float element when the level of water in the evaporating chamber corresponds to the water level set point. The water level set point corresponds, in turn, to an optimal value of the water level in the normal mode of operation of the humidifying device.

In the bottom area, the evaporating chamber has a contact surface for transmitting heat from the heater to the water and hence for the evaporation of the water in the evaporating chamber. The float element regulates the water level in the evaporating chamber by sealing the opening of the water feed means when the water level exceeds the water level set point. The water feed means is connected to a separate water reservoir. When water is needed, the water level in the evaporating chamber drops, and the water feed means is opened. Additional water can thus flow from the water reservoir into the evaporating chamber. An embodiment that is characterized in that means are provided for determining a remaining time during which water will still be present in the evaporating chamber from the signal of the filling level indicator and a signal of a flow sensor and for generating a corresponding output signal for display and for triggering an alarm is significant for recognizing an empty evaporating chamber in a timely manner. The user can thus be informed of a remaining time during which water will still be present in the evaporating chamber in a timely manner and replace or refill the water reservoir within this time to guarantee stable respiration operation. The flow sensor is now preferably arranged at the breathing gas outlet channel. As an alternative hereto, the flow sensor may be arranged in the vicinity of the fan, and the signal of the flow sensor is made available by the fan of the humidifying device via a data interface.

An embodiment is significant in light of disturbances in the closing of the float element, which embodiment is characterized in that a second float element and a second filling level indicator are provided in the evaporating chamber, the second float element being able to be moved in the evaporating chamber above the level of the water level set point and the second filling level indicator is provided to recognize a position of the second float element above the water level set point. Furthermore, means are advantageously provided for generating a corresponding output signal for display and for triggering an alarm from the signal of the second filling level indicator.

Another embodiment is characterized in that the second float element concentrically surrounds the first float element and the second float element advantageously lies on the first float element. A rise in the water level within the evaporating chamber above the water level set point can thus be advantageously recognized by the second filling level indicator as a function of the position of the second float element.

Both the first filling level indicator and the second filling level indicator may be designed as a magnetic sensor array, which comprises a Hall sensor and a magnet made integrally in one piece with the particular float element.

Further, the present invention is characterized by the process for operating a humidifying device for breathing gases, which process has the following process steps: a) feeding of water in a water reservoir into an evaporating chamber, b) blocking of the water feed means at the evaporating chamber by a float element when a water level set point in the evaporating chamber is exceeded, c) heating of the water in the evaporating chamber by a heater, and d) detection of a lowering of the water level from the water level set point with a filling level indicator as a function of the position of the float element.

In another process step, a signal of the filling level indicator and a signal of a flow sensor can be detected, from which a remaining time during which water will still be present in the evaporating chamber is determined in an advantageous manner according to process step d).

In yet another process step, a corresponding output signal is generated for display and for triggering an alarm as a function of the remaining time during which water will still be present in the evaporating chamber.

The present invention will be explained in more detail with reference to the drawings attached, where identical reference numbers designate identical components. The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

DESCRIPTION OF THE PREFERRED EMBODIMENTS

Figure 1:
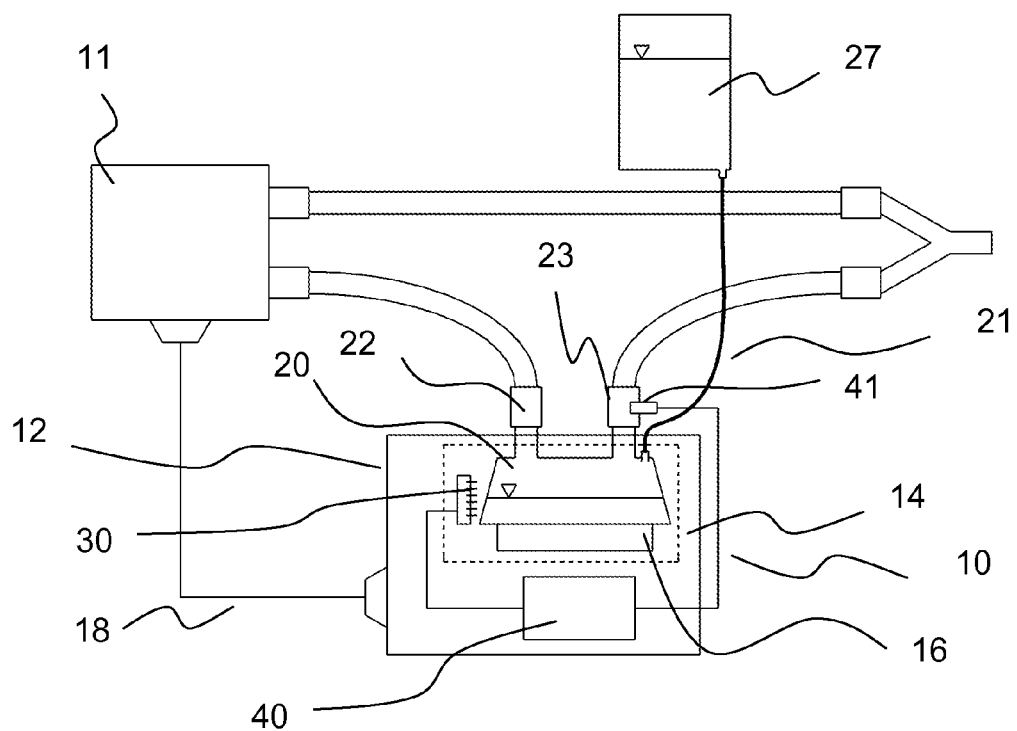
FIG. 1 is a schematic view of a respiration system with a humidifying device according to the present invention.

Referring to the drawings in particular, FIG. 1 shows a respiration system with a humidifying device 10 according to the present invention for enriching the breathing gases with moisture. The respiration system contains a fan 11 for providing breathing gas, which is sent into an evaporating chamber 20 via an inspiration tube through a breathing gas feed channel 22. The breathing gas is heated and humidified above the surface of a quantity of water in evaporating chamber 20. The breathing gas reaches the patient to be respirated through a breathing gas outlet channel 23 of the evaporating chamber 20 via a tube. An expiration tube returns the expired breathing gas to the fan 11. The humidifying device 10 comprises a housing 12 with a recess 14, into which the evaporating chamber 20 can be introduced. The evaporating chamber 20 is in contact in the recess 14 with a heater 16 for heating water of the evaporating chamber 20. Water of a water reservoir 27 enters the evaporating chamber 20 via a water feed means 21. The water flows from the water reservoir 27 arranged above the evaporating chamber 20 into the evaporating chamber 20 through the water feed means under the action of the force of gravity.

Figure 2:
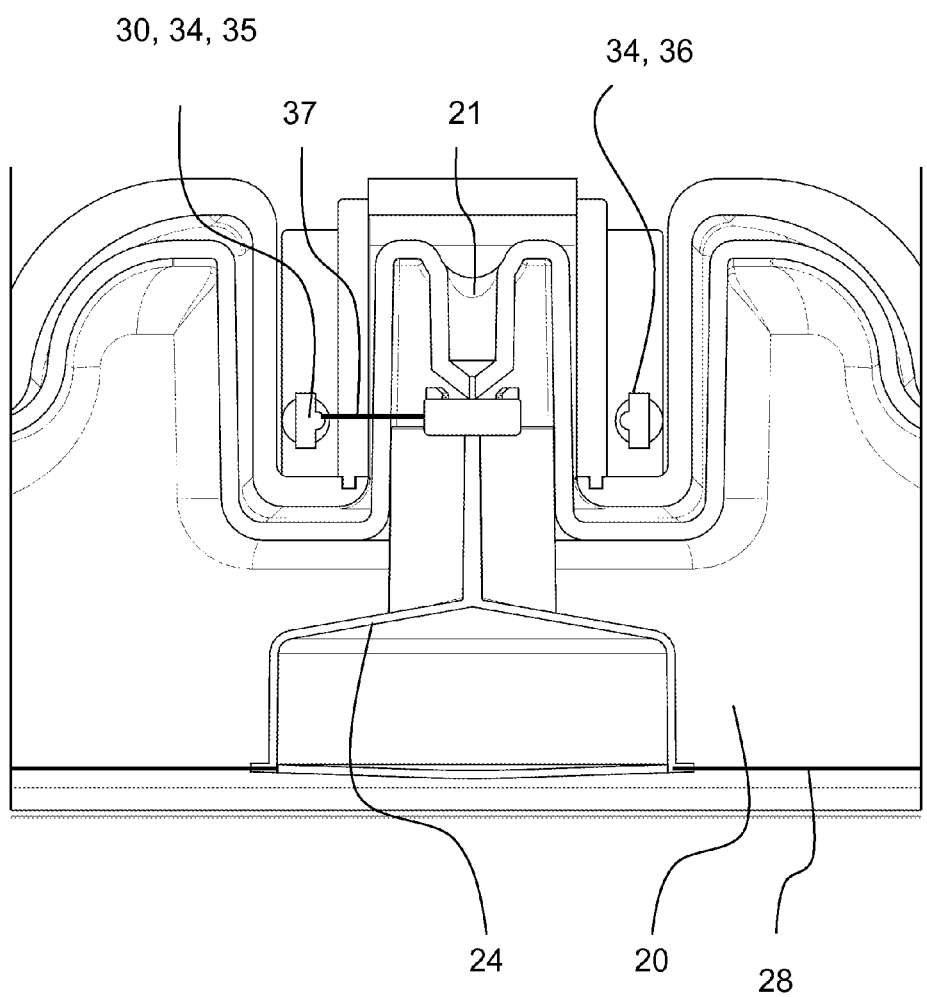
FIG. 2 is a partial detail from a sectional view of the evaporating chamber of the humidifying device according to the present invention.

FIG. 2 shows a partial detail from a sectional view of the evaporating chamber 20 of the humidifying device 10 according to the present invention. Water of the water reservoir 27 enters the evaporating chamber 20 through the water feed means 21. A float element 24, which is guided on the water surface in a floatingly movable manner, is designed to close the water feed means 21 when a water level set point 28 is exceeded. The water level set point 28 corresponds to the level of water in the evaporating chamber during a normal evaporation operation. The float element 24 and the water feed means 21 are designed as a so-called float element valve, wherein the float element 24 and the water feed means 21 regulate the water level in the evaporating chamber by mutual cooperation by sealing the opening of the water feed means 21, especially when the water level set point 28 is reached. If water is needed in the evaporating chamber 20, the water level drops, and the opening of the water feed means 21 is enlarged and additional water can thus flow from the water reservoir 27 into the evaporating chamber 20.

Furthermore, FIG. 2 shows a filling level indicator 30. The filling level indicator 30 is designed as an optical sensor array 34 adapted to the water level set point 28. The optical sensor array 34 comprises a light transmitter 35 and a light receiver 36. The evaporating chamber 20 is made in one piece, preferably from a transparent material. The optical sensor array 34 is provided within the housing 12 of humidifying device 10. The light transmitter 35 and the light receiver 36 are arranged at the evaporating chamber 20 such that a light beam 37 sent by the light transmitter 35 into the evaporating chamber 20 is interrupted by the float element 24 when the level of water in the evaporating chamber 20 corresponds to the water level set point 28. Thus, the light beam 37 does not reach the light receiver 36 at the level of the float element 24, which level corresponds to the water level set point 28. When the water level in the evaporating chamber 20 drops and thus the float element 24 sinks, the float element 24 comes out of the light path of the light transmitter 35, so that the light beam 37 sent by the light transmitter 35 will reach the light receiver 36. A change in the signal of the light receiver 36 signals a lowering of the water to below the water level set point 28 and hence of the water level characterizing the normal operation of the humidifying device 10.

In another embodiment, a calculation means 40 for determining the remaining time during which water will still be present in the evaporating chamber 20 (shown in FIG. 1) is provided. The remaining time during which water will still be present in the evaporating chamber 20 is determined in means 40 from the signal of the filling level indicator 30, a signal of a flow sensor 41 (FIG. 1), which is preferably arranged at the breathing gas outlet channel 23, and in the knowledge of the volume of water below the water level set point 28 in the evaporating chamber 20. Furthermore, a corresponding output signal, which informs the user of the remaining time during which water will still be present in the evaporating chamber 20, is generated for display and for triggering an alarm.

As an alternative to this, flow sensor 41 may also be arranged in the vicinity of fan 11 (not shown), and the signal of sensor 41 is made available in this embodiment by the fan 11 of the humidifying device 10 via a data interface 18 (FIG. 1).

Figure 3:
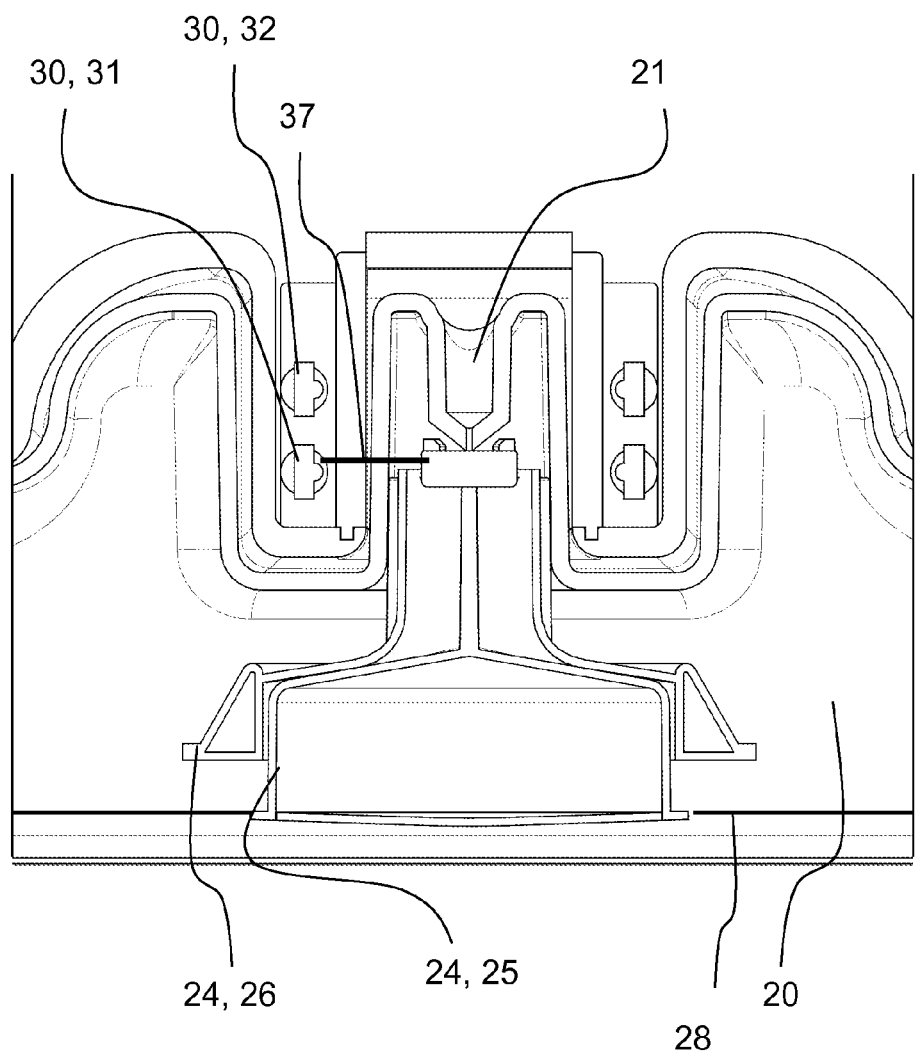
FIG. 3 is a partial detail from a sectional view of the evaporating chamber of the humidifying device according to the present invention with a first filling level indicator and a with a second filling level indicator.

FIG. 3 shows another embodiment of the humidifying device 10 according to the present invention, in which a second float element 26 and a second filling level indicator 32 are provided in the evaporating chamber 20. The embodiment shown is characterized in that the second float element 26 concentrically surrounds the first float element 25 and the second float element 26 advantageously lies on the first float element 25. The second float element 26 does not contact the water surface in this position. In case of a defect in the valve function of the first float element 25 combined with the water feed means 21, the water level in the evaporating chamber 20 may rise continuously. The feed of more water through the water feed means 21 would not be stopped. The consequence would be a critical rise in the water level in the evaporating chamber 20. However, the second float element 26 lying on the first float element 25 floats with the continuously rising water level in the evaporating chamber 20 in the embodiment according to FIG. 3. The second float element 26 in the evaporating chamber can be moved beyond the level of the water level set point 28. If the second float element 26 is moved beyond the water level set point 28, a free light path of the light transmitter-light receiver pair of the second filling level indicator 32, which was hitherto free, is shadowed by the second float element 26. Means are provided in this embodiment for generating a corresponding output signal from the signal of the second filling level indicator 32 for display and for triggering an alarm in case of this malfunction of the first float element 25.

Figure 4:
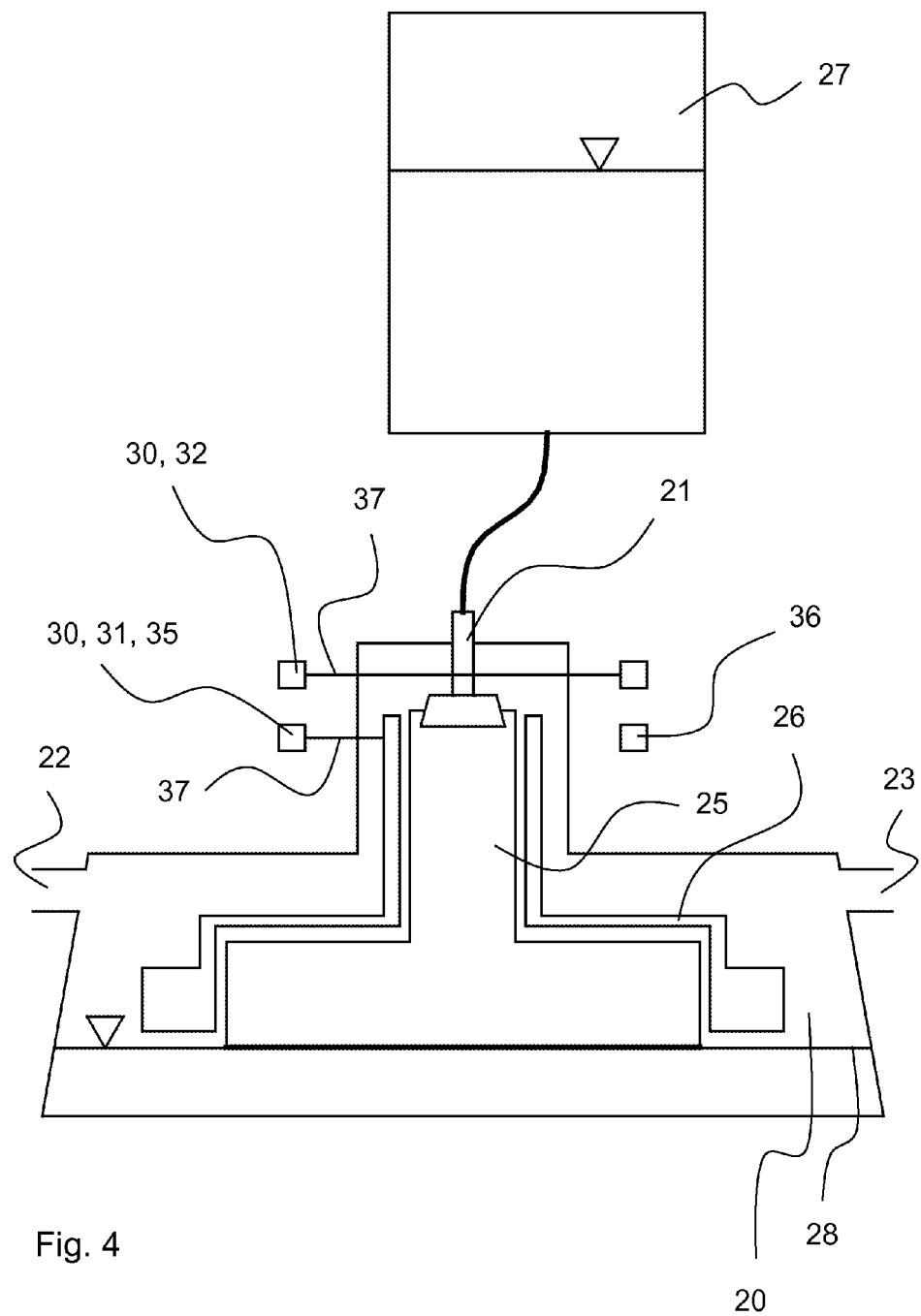
FIG. 4 is a schematic view of the evaporating chamber with water reservoir in the "normal operation" state.

FIG. 4 shows a schematic view of the evaporating chamber 20 of the humidifying device 10 according to the present invention with a water reservoir 27 in the "normal operation" state. The evaporating chamber 20 has in the bottom area a contact surface for transmitting heat from heater 16 (FIG. 1) to the water. The water in the evaporating chamber 20 evaporates due to the heat of heater 16. The first float element 26 regulates the water level in evaporating chamber 20 by sealing the opening of the water feed means 21 when the water level exceeds the water level set point 28. The water feed means 21 is connected to a separate water reservoir 27. When water is needed, the water level drops in evaporating chamber 20, and the water feed means 21 is opened. Additional water can thus flow from the water reservoir 27 into the evaporating chamber 20. The first float element 25 floats on the water surface in the evaporating chamber 20 filled with water. In an initial state of an empty evaporating chamber 20, water is fed by the water feed means 21 from a water reservoir 27 until the first float element 25 interrupts the feed of water by pressing the water feed means 21. The light beam 37 of light transmitter 35 is interrupted by the first float element 25 in this state of "normal operation," so that light beam 37 does not reach the light receiver 36. A light beam 37 generated by the second filling level indicator is not interrupted.

Figure 5:
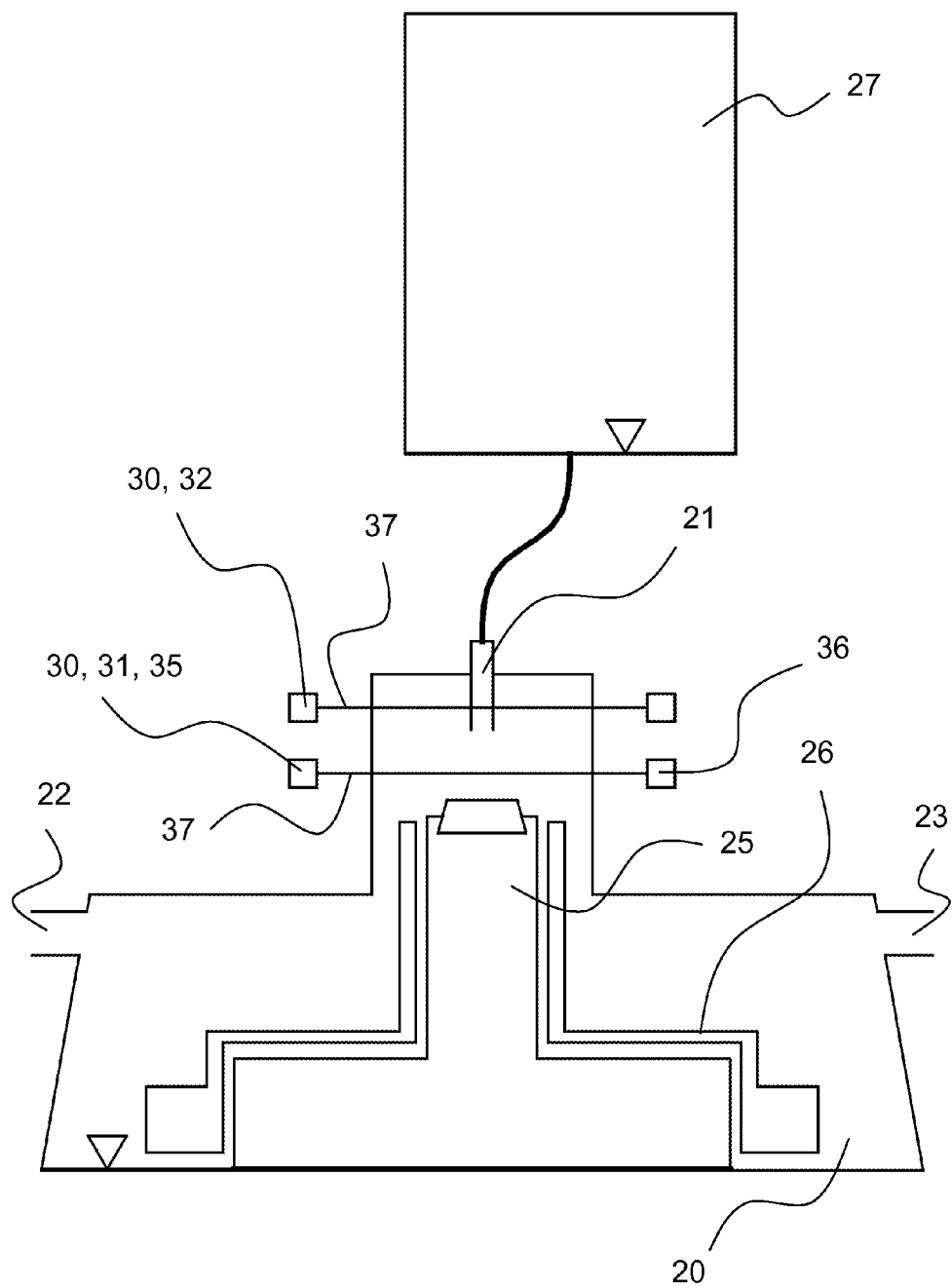
FIG. 5 is a schematic view of the evaporating chamber with water reservoir in the "no water" state.

FIG. 5 shows a schematic view of the evaporating chamber 20 of the humidifying device 10 according to the present invention in the "no water" state. The first float element 25 is now below the water level set point 28. A light beam 37 of the optical sensor array 34 of the first filling level indicator 31, which said light beam is sent by light transmitter 35, reaches the light receiver 36 in the "no water" state. A means 40, in which a remaining time during which water will still be present in the evaporating chamber 20 is determined (not shown in FIG. 5) from the signal of the first filling level indicator 31 and a signal of a flow sensor 41 preferably arranged at the breathing gas outlet channel 23, is provided for recognizing the "no water" state of the evaporating chamber 20 in a timely manner. Furthermore, a corresponding output signal is generated for display and for triggering an alarm. The user can thus be informed of a remaining time during which water will still be present in the evaporating chamber 20 in a timely manner and the water reservoir 27 can be replaced or water can be filled into the water reservoir 27 during this remaining time.

Figure 6:
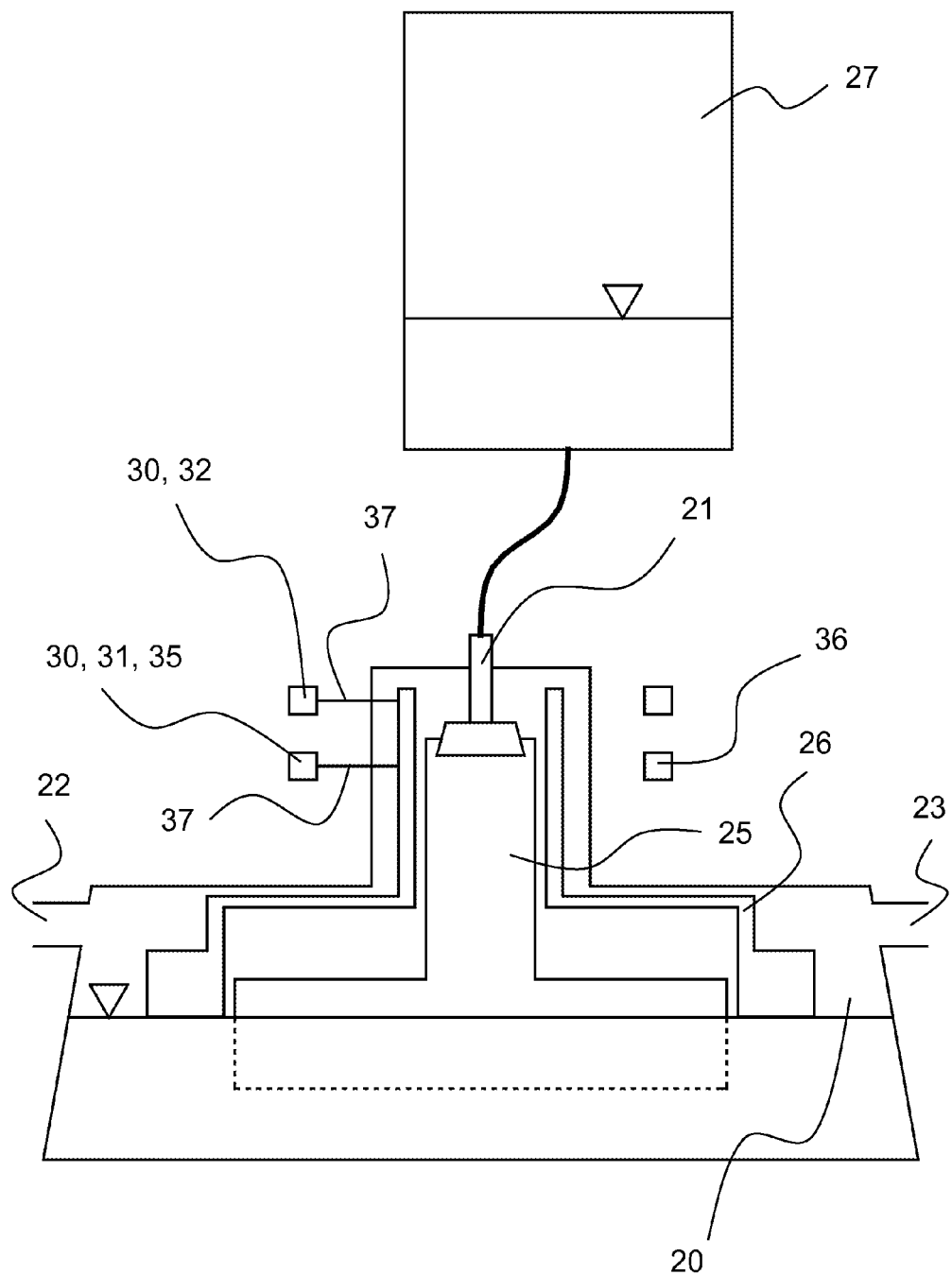
FIG. 6 is a schematic view of the evaporating chamber with water reservoir in the "defective dispensing valve" state.

The state shown in FIG. 6 is significant in light of disturbances in the closing of the float element, which embodiment is characterized in that a second float element 26 and a second filling level indicator 32 are provided in the evaporating chamber 20, wherein the second float element 26 can be moved in the evaporating chamber 20 above the level of the water level set point 28 and the second filling level indicator 32 is provided to recognize a position of the second float element 26 above the water level set point 28. An error has thus developed in the cooperation of the first float element 25 with the water feed means 21 in FIG. 6, so that the water level in the evaporating chamber 26 rises continuously. As a result, the second float element 26 rises and a light beam 37 of the second filling level indicator 32 is interrupted. A critical rise of the water in the evaporating chamber 20 above the water level set point 28 can thus be recognized depending on the position of the second float element 26. Furthermore, means are advantageously provided for generating a corresponding output signal for display and for triggering an alarm (not shown) from the signal of the second filling level indicator 32.

Both the first and second filling level indicators 31 and 32 may be designed as a magnetic sensor array, which comprises a Hall sensor and a magnet made integrally in one piece with the particular float element.

While the present invention has been described with reference to the preferred exemplary embodiments, various changes and modifications are clear to the person skilled in the art. All these changes and modifications will fall within the scope of protection offered by the attached claims. While specific embodiments of the invention have been described in detail to illustrate the application of the principles of the invention, it will be understood that the invention may be embodied otherwise without departing from such principles.

LIST OF REFERENCE NUMBERS

10 Humidifying device
11 Fan
12 Housing
14 Recess
16 Heater
18 Data interface
20 Evaporating chamber 21 Water feed means
22 Breathing gas feed channel
23 Breathing gas outlet channel
24 Float element
25 First float element
26 Second float element
27 Water reservoir
28 Water level set point
30 Filling level indicator
31 First filling level indicator
32 Second filling level indicator
34 Optical sensor array
35 Light transmitter
36 Light receiver
37 Light beam
40 Means for determining the remaining time
41 Flow sensor

What is claimed is:

1. A humidifying device for breathing gas, the humidifying device comprising:
    a housing with a recess;
    a water reservoir;
    a heater;
    an evaporating chamber with a water feed, a breathing gas feed channel, a breathing gas outlet channel, a float element positioned directly below said water feed and a filling level indicator, said float element comprising a float element surface, said evaporating chamber being introduced at least partially into said recess and in contact with said heater for heating water and receiving water from said water reservoir through said water feed, said float element being guided in a floatingly movable manner on the water and said float element closing the water feed above a water level set point in said evaporating chamber, said filling level indicator recognizing a drop of the water level from the water level set point as a function of a position of said float element, wherein breathing gas is delivered to a patient via at least said breathing gas outlet channel, said float element surface rising and falling with said water level, said float element surface being in direct contact with said water feed with said water level being above said water level set point.

2. A humidifying device in accordance with claim 1, wherein the evaporating chamber is made in one piece from a transparent material.

3. A humidifying device in accordance with claim 1, wherein said filling level indicator comprises an optical sensor array adapted to the water level set point, said optical sensor array comprising a light transmitter and a light receiver.

4. A humidifying device in accordance with claim 3, wherein the optical sensor array is arranged outside the evaporating chamber and is set such that a light beam sent by said light transmitter into said evaporating chamber is interrupted by said float element when the level of the water in the evaporating chamber reaches the water level set point.

5. A humidifying device in accordance with claim 1, wherein said filling level indicator comprises a magnetic sensor array adapted to the water level set point, said magnetic sensor array comprising a Hall sensor and a magnet made integrally in one piece with said float element.

6. A humidifying device in accordance with claim 1, further comprising:
    a flow sensor; and
    a remaining time means for generating a remaining time during which water will still be present in said evaporating chamber and for generating a corresponding output signal for display and for triggering an alarm from a signal of said filling level indicator and a signal of said flow sensor.

7. A humidifying device in accordance with claim 1, further comprising:
    a second float element in said evaporating chamber;
    a second filling level indicator in said evaporating chamber, wherein said second float element can be moved above a level of the water level set point in said evaporating chamber and said second filling level indicator is provided to recognize a position of said second float element above said water level set point.

8. A humidifying device in accordance with claim 7, further comprising signal means for generating a corresponding output signal for display and for triggering an alarm from a signal of said second filling level indicator.

9. A humidifying device in accordance with claim 8, wherein said second float element concentrically surrounds the first float element.

10. A humidifying device in accordance with claim 9, wherein said second float element lies on said first float element.

11. A process for operating a humidifying device for breathing gases, the process comprising the steps of:
    providing a humidifying device with a housing with a recess, a water reservoir, a heater and an evaporating chamber introduced at least partially into the recess, the evaporating chamber having a water feed, a breathing gas feed channel, a breathing gas outlet channel, a float element and a filling level indicator, said float element being located at a position below said water feed, said float element comprising a float element surface, said float element surface rising and falling based on a level of water in said evaporating chamber, wherein breathing gas is supplied to a patient via at least said breathing gas outlet channel;
    feeding water from the water reservoir into the evaporating chamber;
    blocking the water feed to the evaporating chamber with said float element surface when a water level set point is exceeded in the evaporating chamber, wherein said float element surface is in direct contact with said water feed when the water level set point is exceeded in the evaporating chamber;
    heating of the water in the evaporating chamber by the heater; and
    detecting a drop in the water level from a water level set point with the filling level indicator as a function of the position of float element.

12. A process in accordance with claim 11, wherein a signal of the filling level indicator and a signal of a flow sensor, arranged at the breathing gas outlet channel, are each detected.

13. A process in accordance with claim 12, wherein a remaining time during which water will still be present in the evaporating chamber is determined from the detected signals of the filling level indicator and of the flow sensor.

14. A process in accordance with claim 13, wherein a corresponding output signal is generated for display and for triggering an alarm as a function of the determined remaining time during which water will still be present in the evaporating chamber.

15. A humidifying device for breathing gas, the humidifying device comprising:
    a housing with an evaporating chamber;
    a water reservoir;

a water feed from the water reservoir to the evaporating chamber, the evaporating chamber receiving water from said water reservoir through said water feed;

a heater in contact with said evaporating chamber for heating water in said evaporating chamber;

a breathing gas feed channel connected to said evaporating chamber;

a breathing gas outlet channel connected to said evaporating chamber, wherein a patient is supplied with a breathing gas via at least said breathing gas outlet channel;

a float element guided in a floatingly movable manner on the water and said float element having an integral float portion, said float element being arranged at a position below said water feed, said integral float portion comprising an integral float portion surface, said integral float portion surface rising and falling based on a level of the water in said evaporating chamber, said integral float portion closing the water feed above a water level set point in said evaporating chamber, wherein said integral float portion surface engages said water feed with the level of the water above the water level set point; and a filling level indicator, said filling level indicator recognizing a drop of the water level from the water level set point as a function of a position of said float element.

16. A humidifying device in accordance with claim 15, wherein said filling level indicator comprises an optical sensor array adapted to the water level set point, said optical sensor array comprising a light transmitter and a light receiver.

17. A humidifying device in accordance with claim 16, wherein the optical sensor array is arranged outside the evaporating chamber and is set such that a light beam sent by said light transmitter into said evaporating chamber is interrupted by the float element when the level of the water in said evaporating chamber reaches the water level set point.

18. A humidifying device in accordance with claim 15, wherein said filling level indicator comprises a magnetic sensor array adapted to the water level set point, said magnetic sensor array comprising a Hall sensor and a magnet made integrally in one piece with said float element.

19. A humidifying device in accordance with claim 15, further comprising:

a flow sensor; and a remaining time calculation means receiving a signal of said filling level indicator and a signal of said flow sensor for calculating a remaining time during which water will still be present in said evaporating chamber upon a drop of the water level from the water level set point based upon said flow sensor and for generating a corresponding output signal for display and for triggering an alarm.

20. A humidifying device in accordance with claim 19, further comprising a second float element in said evaporating chamber;

a second filling level indicator in said evaporating chamber, wherein said second float element can be moved above a level of the water level set point in said evaporating chamber and said second filling level indicator is provided to recognize a position of said second float element above said water level set point.

21. A humidifying device for breathing gas, the humidifying device comprising:

a housing with a recess;

a water reservoir;

a heater;

an evaporating chamber with a water feed, a breathing gas feed channel, a breathing gas outlet channel, a float element and a filling level indicator, said evaporating chamber being introduced at least partially into said recess and in contact with said heater for heating water and receiving water from said water reservoir through said water feed, said float element being guided in a floatingly movable manner on the water and closing the water feed above a water level set point in said evaporating chamber, said filling level indicator recognizing a drop of the water level from the water level set point as a function of a position of said float element;

a flow sensor; and a remaining time means for generating a remaining time during which water will still be present in said evaporating chamber and for generating a corresponding output signal for display and for triggering an alarm from a signal of said filling level indicator and a signal of said flow sensor.

22. A humidifying device for breathing gas, the humidifying device comprising:

a housing with a recess;

a water reservoir;

a heater;

an evaporating chamber with a water feed, a breathing gas feed channel, a breathing gas outlet channel, a float element and a filling level indicator, said evaporating chamber being introduced at least partially into said recess and in contact with said heater for heating water and receiving water from said water reservoir through said water feed, said float element being guided in a floatingly movable manner on the water and closing the water feed above a water level set point in said evaporating chamber, said filling level indicator recognizing a drop of the water level from the water level set point as a function of a position of said float element;

a second float element in said evaporating chamber; and a second filling level indicator in said evaporating chamber, wherein said second float element can be moved above a level of the water level set point in said evaporating chamber and said second filling level indicator is provided to recognize a position of said second float element above said water level set point.

23. A process for operating a humidifying device for breathing gases, the process comprising the steps of:

providing a humidifying device with a housing with a recess, a water reservoir, a heater and an evaporating chamber introduced at least partially into the recess, the evaporating chamber having a water feed, a breathing gas feed channel, a breathing gas outlet channel, a float element and a filling level indicator;

feeding water from the water reservoir into the evaporating chamber;

blocking the water feed to the evaporating chamber by the float element when a water level set point is exceeded in the evaporating chamber;

heating of the water in the evaporating chamber by the heater; and detecting a drop in the water level from a water level set point with the filling level indicator as a function of the position of float element, wherein a signal of the filling level indicator and a signal of a flow sensor, arranged at the breathing gas outlet channel, are each detected, wherein a remaining time during which water will still be present in the evaporating chamber is determined from the detected signals of the filling level indicator and of the flow sensor.

24. A humidifying device for breathing gas, the humidifying device comprising:

a housing with an evaporating chamber;

a water reservoir;

a water feed from the water reservoir to the evaporating chamber, the evaporating chamber receiving water from said water reservoir through said water feed;

a heater in contact with said evaporating chamber for heating water in said evaporating chamber;

a breathing gas feed channel connected to said evaporating chamber;

a breathing gas outlet channel connected to said evaporating chamber;

a float element guided in a floatingly movable manner closing the water feed above a water level set point in said evaporating chamber;

a filling level indicator, said filling level indicator recognizing a drop of the water level from the water level set point as a function of a position of said float element;

a flow sensor; and a remaining time calculation means receiving a signal of said filling level indicator and a signal of said flow sensor for calculating a remaining time during which water will still be present in said evaporating chamber upon a drop of the water level from the water level set point based upon said flow sensor and for generating a corresponding output signal for display and for triggering an alarm.

25. A humidifying device in accordance with claim 24, further comprising a second float element in said evaporating chamber;

a second filling level indicator in said evaporating chamber, wherein said second float element can be moved above a level of the water level set point in said evaporating chamber and said second filling level indicator is provided to recognize a position of said second float element above said water level set point.

* * * * *